United States Patent [19]
Ayukawa

[11] Patent Number: 4,508,707
[45] Date of Patent: Apr. 2, 1985

[54] HAIR TONIC COMPOSITION

[75] Inventor: Taizo Ayukawa, Tokyo, Japan

[73] Assignees: Kakudai Shosan Kabushiki Kaisha; Taizo Ayukawa, both of Tokyo, Japan

[21] Appl. No.: 439,216

[22] Filed: Nov. 4, 1982

[30] Foreign Application Priority Data

Nov. 9, 1981 [JP] Japan .................. 56-179195

[51] Int. Cl.³ .............................. A61K 7/06
[52] U.S. Cl. .................. 424/70; 424/DIG. 4; 424/94; 514/468
[58] Field of Search .............. 424/70, DIG. 4, 94, 424/279

[56] References Cited

PUBLICATIONS

Thompson, FDA Consumer 2/1981, vol. 15, No. 1, pp. 10 and 12.
Journal of The Society of Cosmetic Chemists, 6/1963, vol. 14, No. 6, pp. 249 to 259.
The Merck Index, 1976, 9th edition, p. 4251.

Primary Examiner—Dale R. Ore
Attorney, Agent, or Firm—Oblon, Fisher, Spivak, McClelland & Maier

[57] ABSTRACT

A hair tonic composition comprising a gibberellin and an optional proteolytic enzyme as effective ingredients.

4 Claims, No Drawings

HAIR TONIC COMPOSITION

BACKGROUND OF THE INVENTION

This invention relates to a hair tonic composition.

The hair tonic composition is a hair care product which is prepared by adding a variety of ingredients for hair tonic preparations to solvents such as ethanol and water in addition to propylene glycol, perfume, color and the like. The hair tonic composition is intended to afford the following effects: the blood circulation at the scalp is improved to enhance the skin function, whereby the hair roots are activated; the dust and grime on the scalp and hair are removed to prevent the dandruff and itch; and a refreshing feeling is imparted.

While the physiological mechanism with regard to hair health is not apparent in many respects, the following ingredients for hair tonic preparations have been heretofore used:

(1) Hormones such as follicular formone, adrenal cortical hormone and the like;
(2) Vitamins such vitamins E, $B_2$ and $B_6$ and the like;
(3) Amino acids;
(4) Crude drug extracts such as Japanese chirata extract and the like;
(5) Antiphlogistics such as diphenhydramine hydrochloride, glycyrrhizin and the like;
(6) Keratin-solubilizing agents such as lactic acid, resorcinol, salicylic acid and the like;
(7) Scalp-stimulating agents such as benzyl nicotinate, tincture of copricum, nonylic vanilamide, tincture of cantharis and the like;
(8) Germicides such as isopropyl methylphenol, alkyldiaminoethyl glycine hydrochloride solution, p-chloro-m-xylenol, quaternary ammonium salts and the like;
(9) Refrigerants such as menthol and the like; and
(10) Humectants such as glycerin, propylene glycol, sorbitol, sodium dl-pyrrolidonecarboxylate and the like.

However, because the use of a large amount of certain ingredients for hair tonic preparations such as hormones, germicides and scalp-stimulating agents may cause drawbacks with regard to safety, it is strictly required that the amount of such ingredients incorporated into the hair tonic composition be accurately adjusted. Further, certain ingredients for hair tonic preparations are not entirely satisfactory with respect to prevention of hair loss as well as hair sprouting—and hair growth—promoting effects.

I have made extensive studies in order to overcome the drawbacks accompanying such prior art hair tonic compositions.

SUMMARY OF THE INVENTION

It is an object of the present invention to provide a hair tonic composition which is safe and which has various advantages such as the promotion of hair care; and the prevention of the dandruff and itch.

A hair tonic composition according to the present invention comprises a gibberellin as an effective ingredient.

Further, a hair tonic composition according to the present invention comprises a gibberellin and a proteolytic enzyme as effective ingredients.

DETAILED DESCRIPTION OF THE INVENTION

A gibberellin is a general term for growth-promoting materials of higher plants which are prepared by Gibberella fugikuroi. About 13 gibberellines including gibberellines $A_1$, $A_2$, $A_3$, $A_3'$ and $A_4$ having the following structural formulae are currently known.

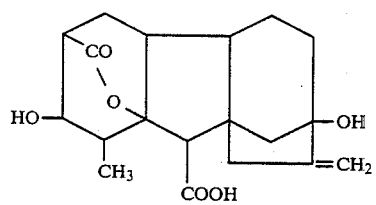

Gibberellin $A_1$

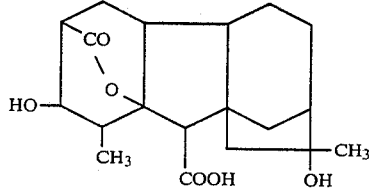

Gibberellin $A_2$

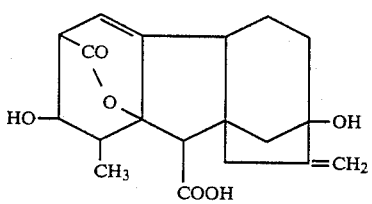

Gibberellin $A_3$

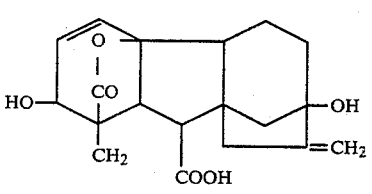

Gibberellin $A_3'$

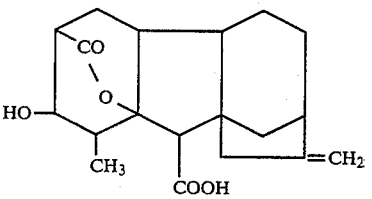

Gibberellin $A_4$

While the gibberellin has been heretofore used primarily as a plant growth regulator in order to increase agricultural products or improve the quality thereof (for example, the formation of seedless grapes, the plumpness of sarcocarp or the plumpness of a cucumber fruit), it was not known that the prevention dandruff and itch could be obtained by using it in a hair tonic composition.

A gibberellin for use herein is present in the hair tonic composition at a level of from 0.001% to 5% by weight, preferably from 0.05% to 1.0% by weight.

A proteolytic enzyme which can be optionally used herein may be of either animal origin or plant origin. The proteolytic enzyme derived from a plant is preferred. Examples of vegetable proteolytic enzymes suitable for use herein are papain obtained from a papaya latex, bromelin obtained from a latex of *Ananas comosus Merr.*, and ficin obtained from a latex of *Ficus carica L.* Among animal proteolytic enzymes suitable for use herein are included pepsin obtained from gastric juice of higher animals, trypsin and chymotrypsin obtained from pancreatic juice of higher animals, and cathepsin obtained from animal tissues.

A mixture of the gibberellin and the proteolytic enzyme is present in the hair tonic composition of the present invention at a level of from 0.001% to 5.0% by weight, preferably from 0.001% to 1.0% by weight, and more preferably from 0.01% to 0.1% by weight. The ratio of the gibberellin to the proteolytic enzyme is from 1:10 to 10:1, preferably from 1:5 to 5:1.

In addition to the gibberellin and the proteolytic enzyme, the hair tonic composition according to the present invention can contain ingredients conventionally used in hair tonic compositions. Examples of such optional ingredients are solvents such as purified water and ethanol; refrigerants such as menthol; humectants such as propylene glycol, glycerin and sorbitol; keratin-solubilizing agents such as lactic acid, resorcinol and salicylic acid; ethers such as polyoxyethylene oleyl ether and polyoxyethylene lauryl ether; vegetable oils such as olive oil and castor oil; higher alcohols such as cetyl alcohol and oleyl alcohol; hydrocarbons such as liquid paraffin and acetone; vitamin; perfumes, coloring agents; and preservatives. If necessary, ingredients for hair tonic preparations such as hormones, germicides, anti-phlogistics, scalp-stimulating agents and the like can be incorporated in the hair tonic composition of the present invention.

The hair tonic composition according to the present invention can be prepared in accordance with the general process for preparing an ordinary hair tonic composition except that the gibberellin and the optional proteolytic enzyme are incorporated therein.

The following examples illustrate the present invention but are not intended to limit the scope thereof. Throughout these examples, quantities expressed in "parts" are by weight.

EXAMPLE I

A hair tonic composition containing the following ingredients was prepared.

| | |
|---|---|
| Ethanol | 70 parts |
| Vitamin E | 0.05 parts |
| Vitamin B$_2$ | 0.05 parts |
| Propylene glycol | 3 parts |
| Menthol | 0.1 parts |
| Resorcinol | 0.1 parts |
| Gibberellin | 0.1 parts |
| Color, perfume | q.s. |
| Purified water | 30 parts |

When this hair tonic composition was applied daily onto scalps over 3 months, dandruff was effectively prevented.

EXAMPLE II

A hair tonic composition containing the following ingredients was prepared.

| | |
|---|---|
| Ethanol | 70 parts |
| Vitamin E | 0.1 parts |
| Propylene glycol | 2.5 parts |
| Menthol | 0.1 parts |
| Diphenhydramine hydrochloride | 0.01 parts |
| Lactic acid | 0.1 parts |
| Gibberellin | 0.05 parts |
| Color, perfume | q.s |
| Purified water | 30 parts |

When this hair tonic composition was applied daily onto scalps over 3 months, dandruff and itch were effectively prevented.

EXAMPLE III

A hair tonic composition containing the following ingredients was prepared.

| | |
|---|---|
| Ethanol | 80 parts |
| Castor oil | 5 parts |
| Menthol | 0.1 parts |
| Resorcinol | 0.1 parts |
| Tincture of capsicum | 0.2 parts |
| Glycerin | 0.5 parts |
| Gibberellin | 0.2 parts |
| Color, perfume | q.s. |
| Purified water | 20 parts |

When this hair tonic composition was applied daily onto scalps over 3 months, dandruff and itch were prevented.

EXAMPLE IV

A hair tonic composition containing the following ingredients was prepared.

| | |
|---|---|
| Ethanol | 70 parts |
| Vitamin E | 0.05 parts |
| Vitamin B$_2$ | 0.05 parts |
| Propylene glycol | 3 parts |
| Menthol | 0.1 parts |
| Resorcinol | 0.1 parts |
| Gibberellin | 0.05 parts |
| Papain | 0.05 parts |
| Color, perfume | q.s. |
| Purified water | 30 parts |

When this hair tonic composition was applied onto hair, dandruff was effectively prevented.

EXAMPLE V

A hair tonic composition containing the following ingredients was prepared.

| | |
|---|---|
| Ethanol | 70 parts |
| Vitamin E | 0.1 parts |
| Propylene glycol | 2.5 parts |
| Menthol | 0.1 parts |
| Diphenhydramine hydrochloride | 0.01 parts |
| Lactic acid | 0.1 parts |
| Gibberellin | 0.01 parts |
| Bromelin | 0.02 parts |
| Color, perfume | q.s. |
| Purified water | 30 parts |

When this hair tonic composition was applied onto hair, dandruff and itch were effectively prevented.

EXAMPLE VI

A hair tonic composition containing the following ingredients was prepared.

| | |
|---|---|
| Ethanol | 80 parts |
| Castor oil | 5 parts |
| Menthol | 0.1 parts |
| Resorcinol | 0.1 parts |
| Tincture of capsicum | 0.2 parts |
| Glycerin | 0.5 parts |
| Gibberellin | 0.02 parts |

When this hair tonic composition was applied onto hair, dandruff and itch were effectively prevented.

What is claimed is:

1. A hair tonic composition comprising 0.001% to 5% by weight of a gibberellin, a hair tonic solvent and conventional hair tonic ingredients.

2. A hair tonic composition comprising a gibberellin, a proteolytic enzyme and a hair tonic solvent, wherein a mixture of the gibberellin and the proteolytic enzyme is present in the composition at a level of from 0.001% to 5% by weight.

3. The hair tonic composition of claim 2 wherein the weight ratio of the gibberellin to the proteolytic enzyme is from 1:10 to 10:1.

4. The hair tonic composition of claim 2 wherein the proteolytic enzyme is at least one enzyme selected from the group consisting of papain, bromelin, ficin, pepsin, trypsin, chymotrypsin and cathepsin.

* * * * *